(12) United States Patent
Parker

(10) Patent No.: US 7,922,759 B1
(45) Date of Patent: Apr. 12, 2011

(54) APPARATUS AND METHODS FOR VASCULAR TREATMENT

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1165 days.

(21) Appl. No.: 11/112,663

(22) Filed: Apr. 22, 2005

Related U.S. Application Data

(60) Provisional application No. 60/564,541, filed on Apr. 22, 2004.

(51) Int. Cl.
*A61F 2/06* (2006.01)
*A61M 31/00* (2006.01)

(52) U.S. Cl. .......... 623/1.36; 604/509; 623/903

(58) Field of Classification Search ........... 623/1.11, 623/1.23, 1.41, 1.47, 1.12, 1.13, 1.14, 1.36, 623/903; 606/192, 194, 198, 200; 424/422; 604/506–509
See application file for complete search history.

(56) References Cited

U.S. PATENT DOCUMENTS

| | | | |
|---|---|---|---|
| 4,562,596 A * | 1/1986 | Kornberg | 623/1.32 |
| 4,902,508 A * | 2/1990 | Badylak et al. | 424/423 |
| 5,527,355 A * | 6/1996 | Ahn | 623/1.36 |
| 5,571,171 A * | 11/1996 | Barone et al. | 128/898 |
| 5,591,229 A | 1/1997 | Parodi | |
| 5,728,131 A | 3/1998 | Frantzen et al. | |
| 6,152,956 A | 11/2000 | Pierce | |
| 6,168,579 B1 | 1/2001 | Tsugita | |
| 6,383,171 B1 | 5/2002 | Gifford et al. | |
| 6,592,616 B1 | 7/2003 | Stack et al. | |
| 6,620,148 B1 | 9/2003 | Tsugita | |
| 6,652,554 B1 | 11/2003 | Wholey et al. | |
| 6,656,351 B2 | 12/2003 | Boyle | |
| 2003/0050600 A1 | 3/2003 | Ressemann et al. | |
| 2003/0187493 A1* | 10/2003 | Campbell et al. | 623/1.11 |
| 2003/0191517 A1* | 10/2003 | Osborne et al. | 623/1.13 |
| 2003/0195556 A1 | 10/2003 | Stack et al. | |
| 2003/0212429 A1 | 11/2003 | Keegan et al. | |
| 2005/0043780 A1 | 2/2005 | Gifford et al. | |

FOREIGN PATENT DOCUMENTS

WO  WO 99/45835  9/1999

* cited by examiner

*Primary Examiner* — Nicholas D Lucchesi
*Assistant Examiner* — Nathan R Price
(74) *Attorney, Agent, or Firm* — Woodard, Emhardt, Moriarty, McNett & Henry LLP

(57) ABSTRACT

According to one embodiment there is disclosed a device including a shield member including an ECM material and a retaining member conformable to maintain at least a portion of the shield member in a desired relationship with respect to an area of a blood vessel to be treated or repaired.

16 Claims, 8 Drawing Sheets

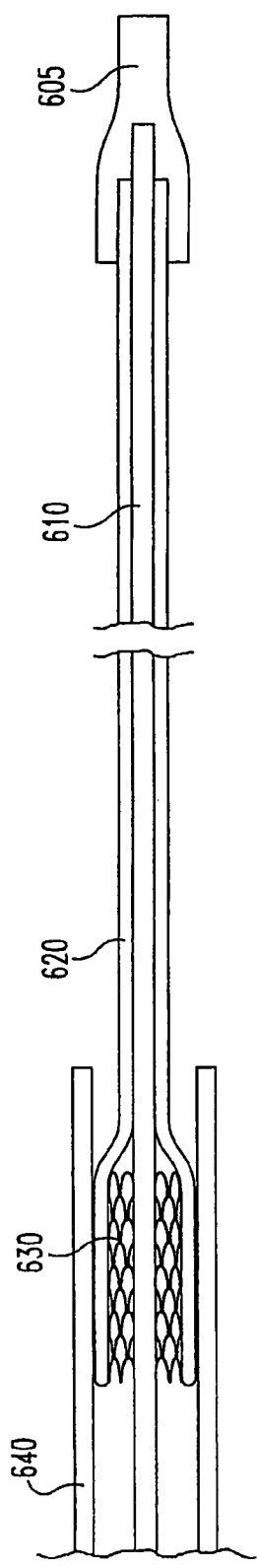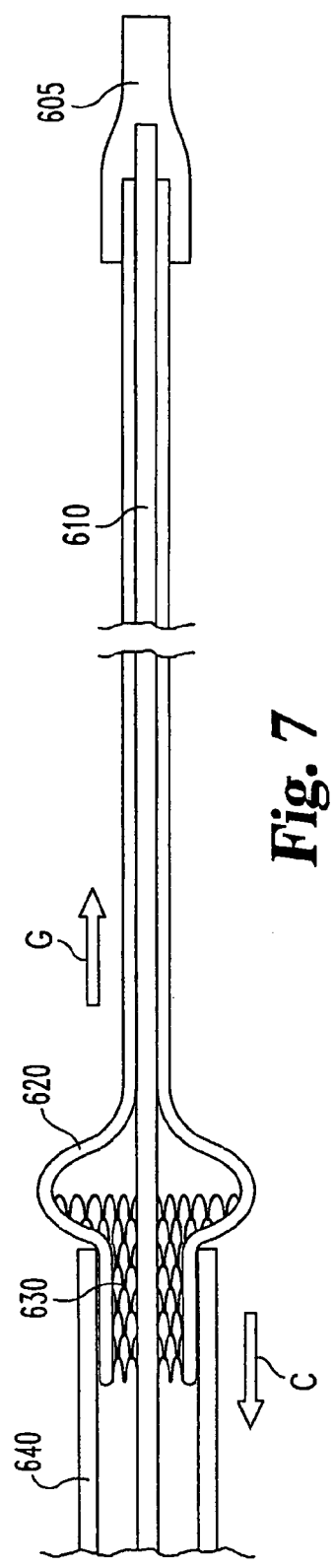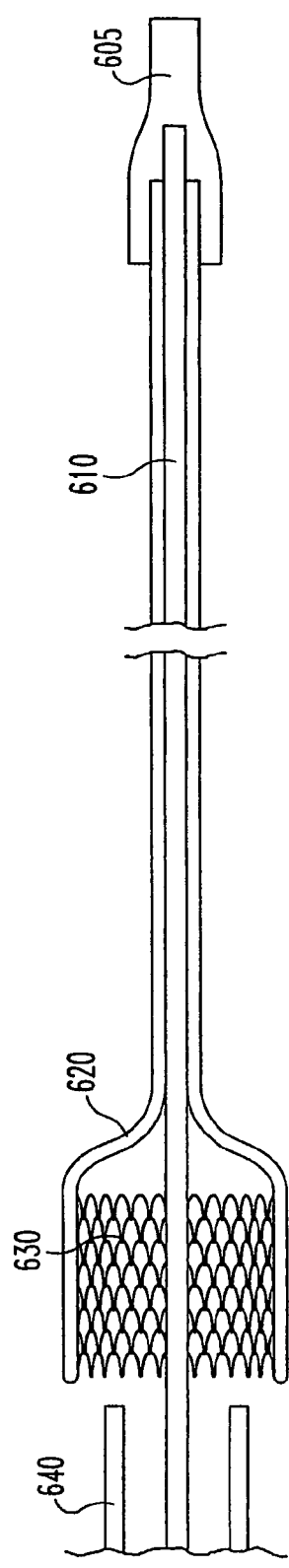

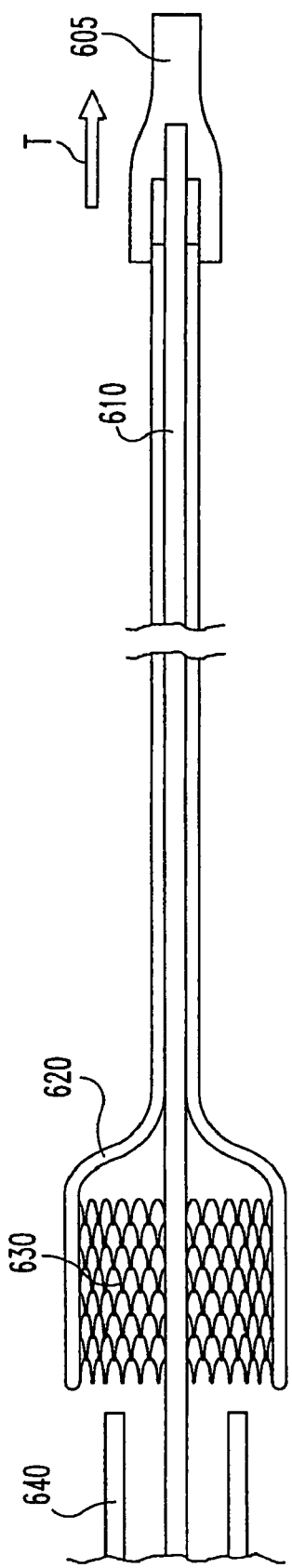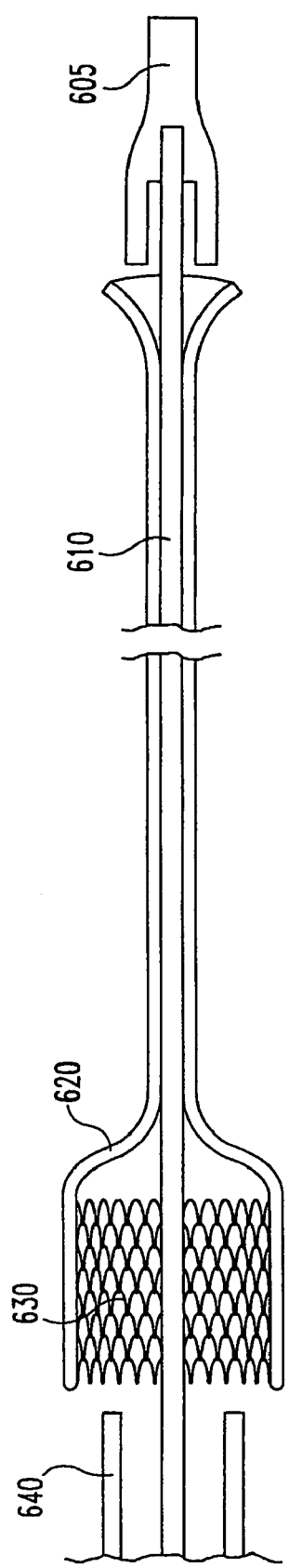

APPARATUS AND METHODS FOR VASCULAR TREATMENT

This application claims the benefit of U.S. Application No. 60/564,541 file Apr. 22, 2004 and the same is hereby incorporated by reference.

BACKGROUND

The present invention relates generally to devices, methods and systems for vascular treatment. One embodiment of the present invention relates to a device including an ECM material section and an associated retention member. The ECM material may be placed in a vascular lumen with at least one portion anchored to a vessel. The apparatus can shield a portion of the vessel and also permit further treatment to that or other area(s). While the invention is described with respect to vascular applications, it may also apply to treatment of the hepatic, urinary, respiratory, digestive or reproductive systems, and other anatomical lumen(s), for example.

Vascular diseases and disorders are widespread health problems affecting many people. There are many chronic and acute diseases and disorders relating to the vascular system including, for example, thrombosis, embolism, aneurysm, atherosclerosis, arterioschlerosis, infarction and still others. Heart attacks and strokes are leading health concerns. Obstruction of blood flow and/or vessel rupture may cause inadequate blood supply the heart, brain and other parts or all of the body. Occlusive diseases involving constriction, narrowing or obstruction of a blood vessel often present serious possibly life-threatening risks. Additionally, complications in vascular treatment(s) may themselves necessitate further treatment. Some such risks include formation of emboli, vessel damage, thrombogenesis, blood loss, hemorrhage, and others. Furthermore, trauma and other injuries may damage the vascular system and often require repair or replacement.

At present, treatment of vascular disease, damage and disorders suffers from limitations, drawbacks and risks. The invention provides unique treatments and solutions to treatment of the foregoing and other problems.

SUMMARY

According to one embodiment of the present invention there is contemplated a method including introducing a device into an organ, the organ having an interior surface and containing a fluid, shielding at least a portion of the interior surface from the fluid and administering additional treatment to at least the shielded portion.

A further embodiment according to the present invention relates to an implantable prosthesis including an ECM material and an anchoring member, wherein the implant is introduceable into a blood vessel in a first state and the anchoring member maintains a portion of the implant in a substantially fixed relationship with the blood vessel in a second state.

Yet another embodiment according to the present invention relates to a device including a buffer member adapted to be introduced into a blood vessel to buffer at least a portion of the blood vessel from blood therein, and a retaining member conformable to maintain at least a portion of the buffer member in contact with a portion of the blood vessel.

Still a further embodiment according to the present invention includes a treatment system including an intraluminal prosthesis including at least a first portion which is secured relative to a flow in the lumen, a second portion which is capable of movement relative to the first portion in a first state and a treatment device inserted into the lumen and positionable to a location adjacent the prosthesis, the device delivering treatment at about the adjacent location, wherein blood flow is substantially unobstructed by the prosthesis.

Yet another embodiment according to the present invention relates to a medical device including a lumen shield of ECM material and an anchor member which is conformable to a retaining position effective to maintain at least a part of the shield in a fixed position with respect to a lumen into which the device has been introduced.

Still a further embodiment according to the present invention relates to an apparatus including a tubular piece formed at least in part of an ECM and a stent at least a part of which is affixed to at least a part of the tubular piece wherein the apparatus is sized to permit introduction into a blood vessel in a first state and is conformable to a second state in which it is effective to shield an interior surface of the blood vessel from the blood flowing therethrough.

Yet a further embodiment according to the present invention relates to a method of treating disease or damage of a blood vessel including sheltering a portion of a luminal surface of the blood vessel from the blood flow therethrough, administering treatment to the blood vessel, and inducing repair or restoration of the blood vessel with an ECM material.

Various embodiments of the present invention provide unique apparatus and methods of treating the vascular system. Still other embodiments, examples and features according to the present invention will be apparent from the following description and claims.

BRIEF DESCRIPTION OF THE DRAWING

FIGS. 2 and 2A illustrate a cross section of an apparatus according to embodiments of the present invention in a blood vessel.

FIG. 6 illustrates a cross section of an apparatus according to one embodiment of the present invention.

FIGS. 7-10 illustrate cross sections of the apparatus of FIG. 6 in other states.

DETAILED DESCRIPTION

Figure 1:
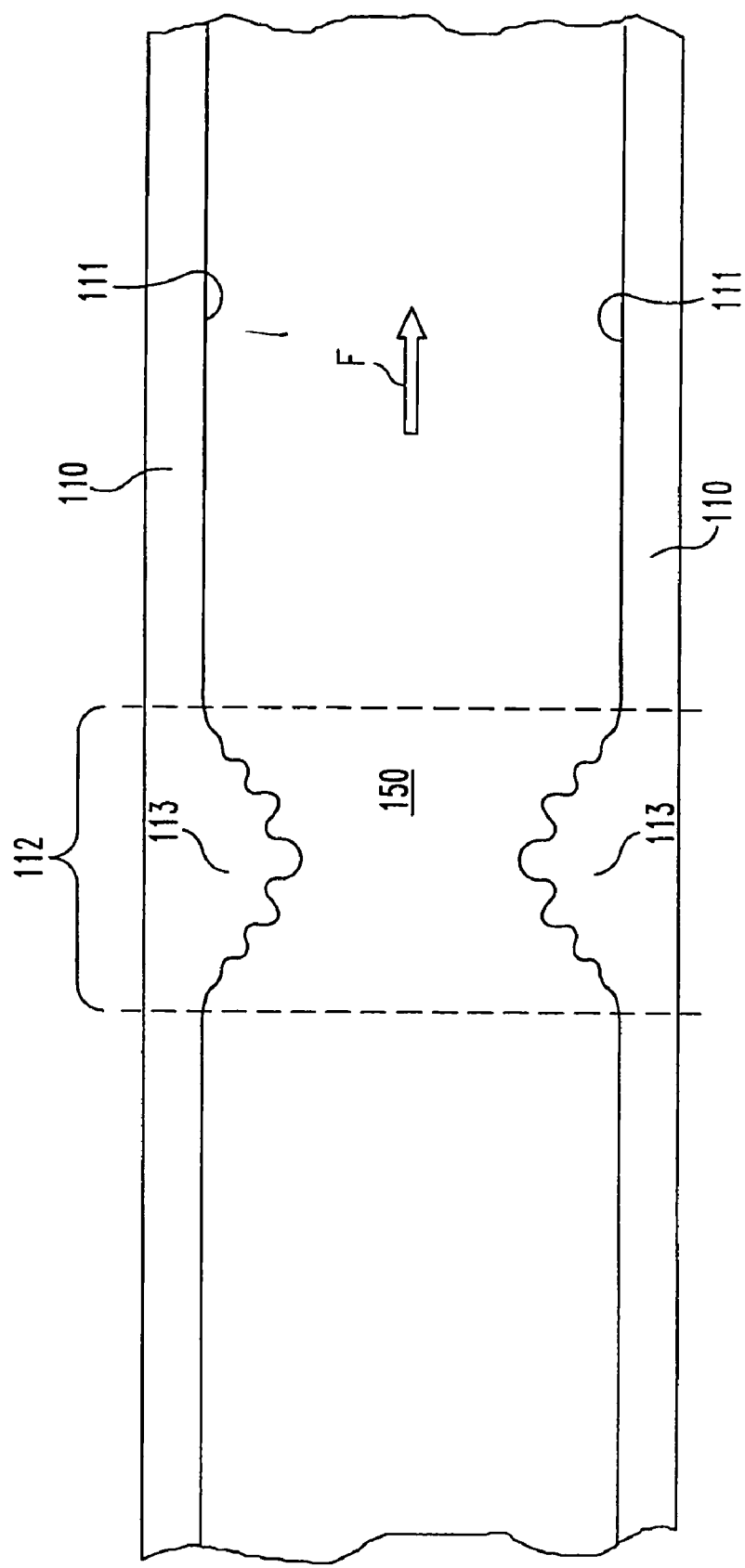
FIG. 1 illustrates a cross section of a stenotic blood vessel.

For the purposes of promoting an understanding of the principles of the invention, reference will now be made to the embodiments illustrated in the drawings and specific language will be used to describe the same. Nevertheless, no limitation of the scope of the invention is intended. Such alterations and further modifications in the illustrated and described embodiments, and such further applications of the principles of the invention as illustrated therein as would occur to one skilled in the art to which the invention relates are contemplated.

With reference to FIG. 1 there is shown an illustrative view of a blood vessel 110 which includes interior surface 111 and lumen 150. Blood flow through vessel 110 is generally in the direction indicated by arrow F and may vary according to physiological conditions. Stenosis 113 is a narrowing or constriction of lumen 150 of vessel 110 in the region generally indicated at 112. The narrowing or constriction of lumen 150 results in reduced blood flow through vessel 110 and increased risk of thrombosis, embolism, and other complications. While stenosis 113 is illustrated, other diseases, damage, or disorders could be present in region 112 or other in other regions. For example, thrombosis, aneurysm, lodged embolism, necrotic tissue, cut or damaged vessel tissue, perforation, and other lesions, disease, disorders or damage including those described above (hereinafter "disease(s)") may all be treated by the present invention. For the sake of brevity, treatment of stenosis is illustrated and described with the understanding that treatment of the aforementioned diseases and others is also contemplated and protected. Furthermore, it should be understood that the term "vascular" includes, without limitation, the vascular, cardiovascular and/or circulatory systems or portions thereof. Further still, it will be understood that present invention may be applied to still other tubular organs, such as the gall bladder, esophagus, kidney, as well as to organs of the renal, urinary, digestive, alimentary, hepatic, reproductive, respiratory, endocrine and other physiological systems.

Figure 2:
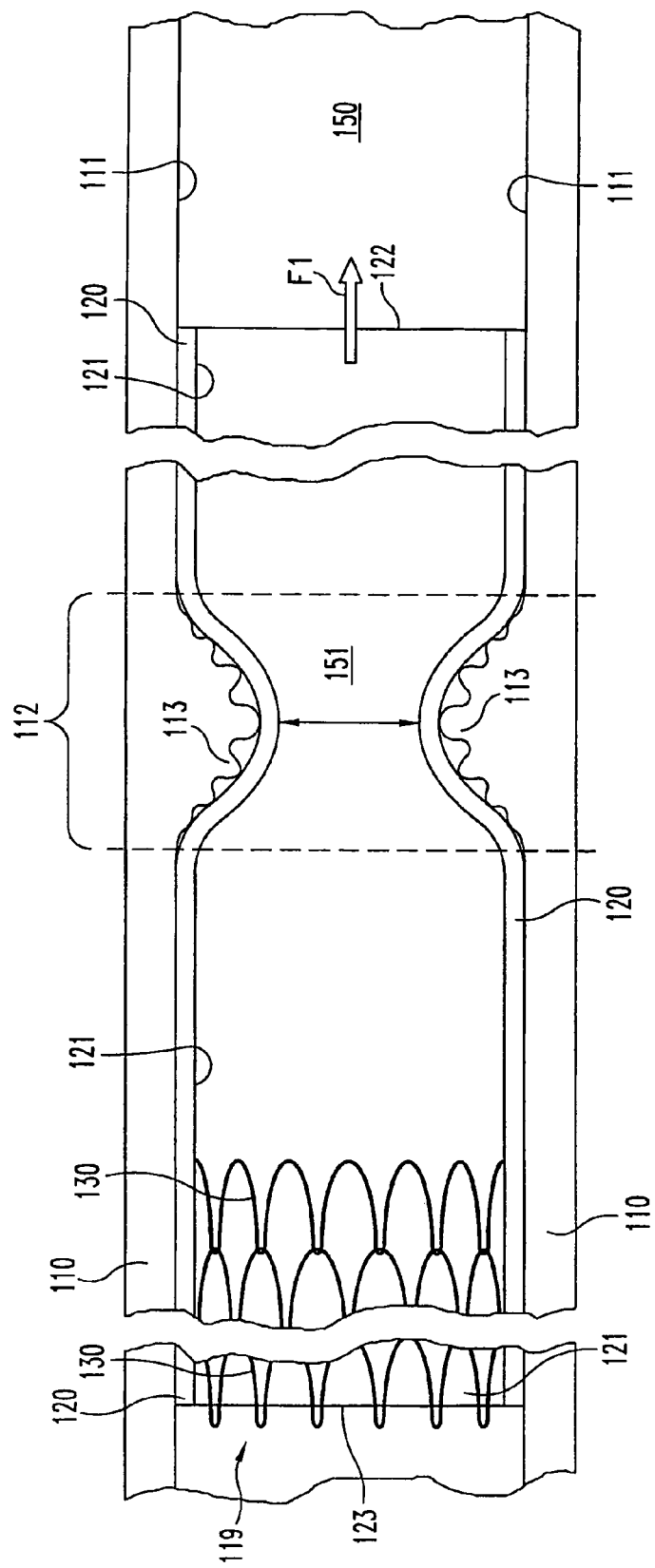
FIG. 2 illustrates

With reference to FIG. 2 there is shown an illustrative view of a device 119 according to one embodiment of the present invention which has been placed in lumen 150 of blood vessel 110. Device 119 includes member 120 and expandable member 130. Device 119 includes member 120 which extends from distal end 122 to proximal end 123. Member 120 includes interior surface 121 and lumen 151.

As illustrated in FIG. 2, member 120 is tubular, however, in other embodiments member 120 could be partially tubular, a split tube, a coil, a roll, an overlapping tube, a strip, overlapping strips, a ribbon, or a patch to name a few examples. Still other embodiments of the present invention contemplate combinations of these and other structures.

Member 120 may include ECM material(s). As used herein, ECM material(s) or extracellular matrix materials refer(s) to a class of biomaterials including, but not limited to, submucosa, mucosa, serosa, pericardium, dermis, fascia, basement membrane, and/or combinations thereof. ECM materials may be derived from various tissue sources including the alimentary, hepatic, respiratory, intestinal, integument, urinary, or genital tracts. ECM materials can be harvested from animals, including, for example, pigs, cattle, sheep, porcine, bovine, ovine or other warm-blooded vertebrates to produce heterologous implants or grafts. Products comprising submucosa tissue derived from porcine small intestine are commercially available ECM materials produced by COOK BIOTECH INCORPORATED of West Lafayette, Ind.

Member 120 can comprise any of the aforementioned ECM materials or other ECM materials. Member 120 can also include 1, 2, 3, 4, 5, 6, 7, 8 or more ECM layers. Further, in some embodiments, member 140 can comprise any devitalized or substantially acellular collagenous matrix, naturally-derived or synthetic, and desirably remodelable. The remainder of the text will refer to ECM material unless specifically stated to the contrary. This will not, however, be limiting of the broader aspects of the invention.

It is also contemplated that member 120 could also include synthetic polymeric material instead of or in addition to ECM material(s). Such synthetic polymeric materials include, but not limited to polytetrafluoroethylene ("PTFE") (including expanded PTFE) and/or polyethylene terephthalate ("PET). Further, the synthetic polymer materials can be either a biostable or a bioabsorbable polymer. Bioabsorbable polymers that could be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. Biostable polymers that could be used include, but are not limited to, polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. The material may be in the form of yarns, fibers, and/or resins, monofilament yarns, high tenacity polyester and others. Further, the present application contemplates other plastic, resin, polymer, woven, and fabric surgical materials, other conventional synthetic surgical materials, and/or combinations of such materials.

It will be appreciated that the length, shape, thickness, layers, composition, orientation, other dimensions and attributes of member 120 may be dictated by the desired treatment. Examples of particularized treatment considerations include: a lesion spanning part of or the entire circumference of a vessel calling for a tubular structure, overlapping tube(s), split tube(s), overlapping strips or other circumference spanning configurations. Varying vessel dimensions may also influence attributes of member 120. For example, an aneurysm may require one or more layers of certain materials to provide adequate strength. The location and nature of vascular disease(s) may also be a factor. Desire for tissue remodeling may suggest use of ECM materials, desire for other characteristics, for example, durability or strength may indicate one or more synthetic materials, and desire for combinations of characteristics may call for hybrid structures. It is also contemplated that member 120 could be one piece, or could include two or more pieces, parts, or units.

With continuing reference to FIG. 2, retention member 130 contacts the interior of member 120 and extends from outside proximal end 123 of member 120 into member 120. Member 130 could also extend from farther outside end 123, from end 123, or from inside end 123. In certain embodiments member 130 could extend substantially the length, the entire length, or more than the entire length of member 120.

Member 130 is shown in an expanded configuration in which it can exert bias toward surface 121 of member 120 and maintain a portion of member 120 against interior surface 111 of blood vessel 110. It is also contemplated that member 130 could contact the interior surface of member 120, be between two layers of a multi-layer member 120, embedded within member 120, attached to the outer surface of member 120, pierce through member 120, be coupled to member 120 by intermediate structure, attached to member 120 using additional fasteners, connectors, glue, adhesive, tape, suture, staples, or other structures.

Figure 2A:
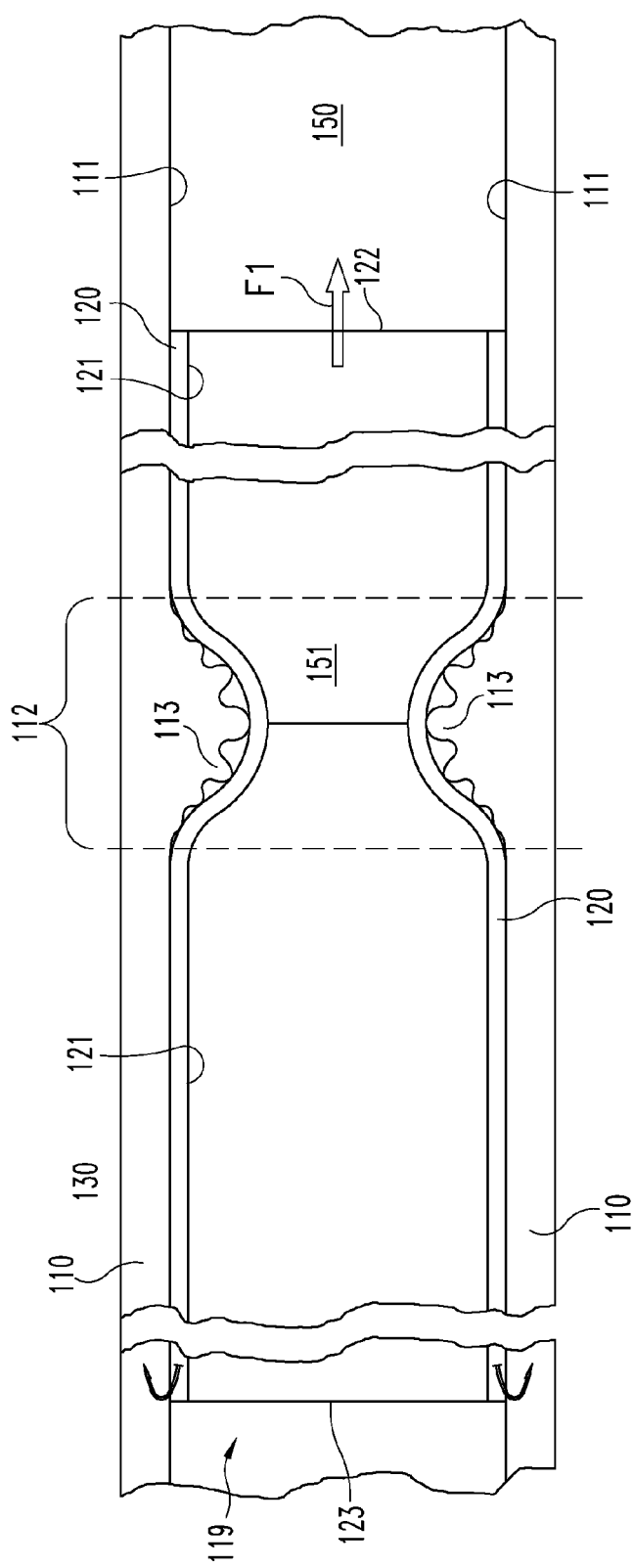

Retention member 130 is illustrated as a self-expanding vascular stent but could also be a balloon expandable vascular stent, or any other structure that is not classified as a stent but capable of being introduced into a blood vessel and maintaining at least a portion of member 120 in a desired position or location. Member 130 could be compressible, flexible, bendable, collapsible, rolled, coiled, or twistable, hinged, jointed or otherwise conformable to permit retention of member 120. Member 120 could also include or consist of barbs or other structures (e.g. FIG. 2A) which perforate part or all of member 120 and/or a vascular structure.

Member 130 is shown as having a particular braided structure, however, it is contemplated that a wide variety of structures could be used. For example, coil structure(s), spiral structure(s), helical structure(s), woven structure(s), other braided structure(s), ring(s), sinusoidal structure(s), Z-shaped structure(s), zig-zag structure(s), closed cell structure(s), open cell structure(s), and other types of vascular stents are contemplated. Furthermore, the material or materials of member 130 could include stainless steel, tantalum, nitinol, platinum, iridium, polymers, niobium, cobalt, molybdenum, drug eluting coating(s), ECM coating(s) and other materials, alloys, or combinations of the foregoing non-limiting examples. Additionally, it is contemplated that one or more other members could be used at various locations in connection with member 120, and could be the same, similar to or different from member 130 including, for example, the variations described above.

As shown in FIG. 2, a portion of member 120 extends beyond member 130 to end 122. This portion of member 120 is maintained against interior surface 111 by hemostatic pressure. As illustrated, member 120 can conform to the shape of interior 111 as well as to the irregularities presented by stenosis 112. Hemostatic pressure may be present within member 120 due to the blood flow therethrough, but in the case of trauma or patient and treatment conditions, for example, wide variation in pressure may exist. Blood flow enters member 120 at end 123 and is routed through lumen 151 of member 120 and out of end 122 in the direction generally indicated by arrow F1. Thus, blood flow is isolated from stenosis 113 and from portions of interior surface 111.

Figure 3:
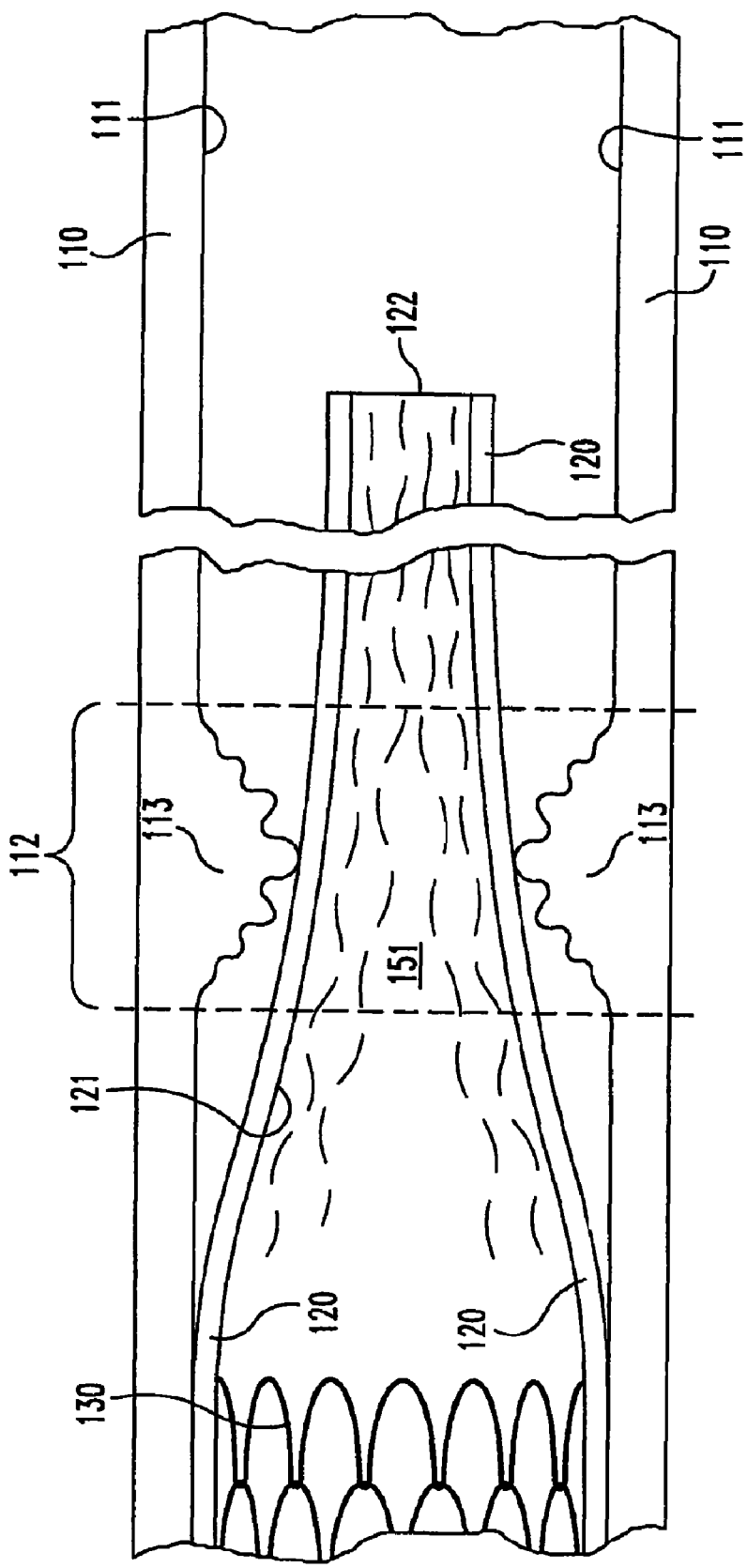
FIG. 3 illustrates a cross section of the apparatus of FIG. 2 in another state.

With reference to FIG. 3 there is shown an illustrative view of the apparatus and blood vessel described above under different environmental conditions. There are shown various attributes described above in connection with FIGS. 1 and 2 indicated with identical reference numerals. In FIG. 3 the fluid or hemostatic pressure of blood in vessel 110 is less than in FIG. 2 and could be neutral or negative as well. Accordingly, there may be less tendency for member 120 to be maintained against interior surface 111 by hemostatic pressure and a portion of member 120 may move to the position illustrated in FIG. 3 or to other positions, or might move minimally or substantially not at all. In other embodiments, member 130 could be differently positioned or proportioned to maintain more or less of member 120 against interior surface 111. In still further embodiments part or all of member 120 need not directly contact the vessel wall, and could be maintained in position by an intermediate structure or structures. Furthermore, in some situations hemostatic pressure and/or properties of member may increase the tendency of member 120 to remain against or adjacent to interior surface 111.

Figure 4:
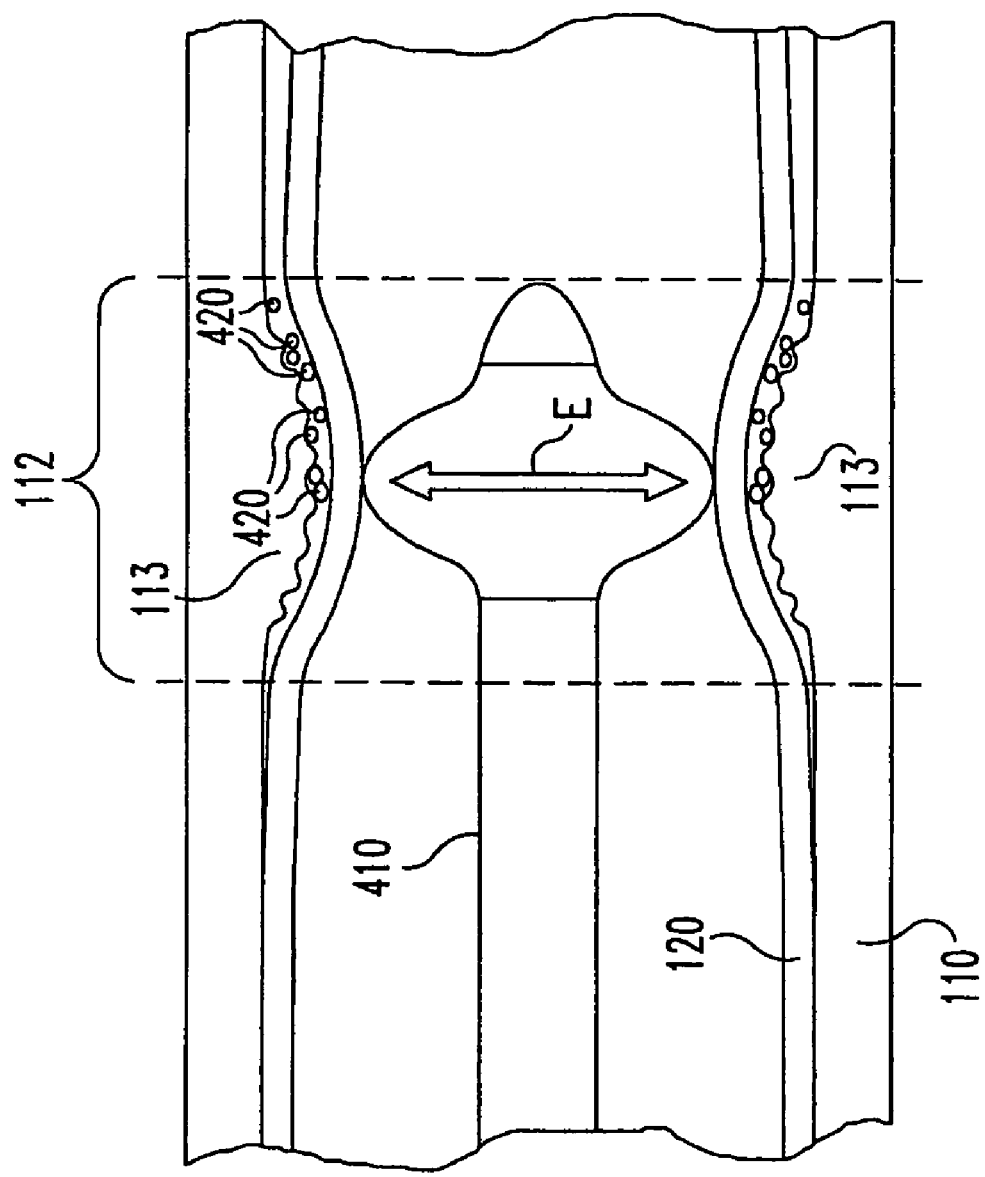
FIG. 4 illustrates a cross section of treatment of stenosis according to one embodiment of the present invention.
Figure 5:
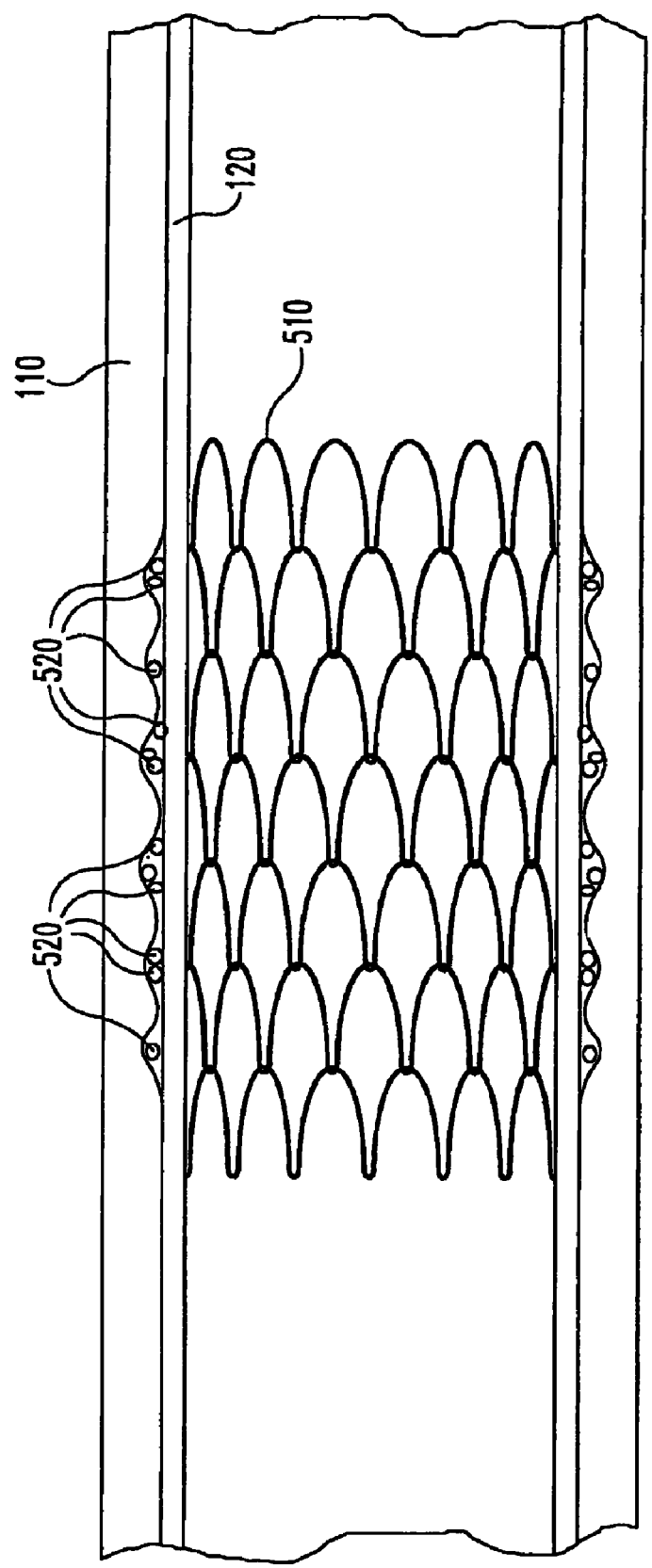
FIG. 5 illustrates a cross section of treatment of stenosis according to one embodiment of the present invention.

FIGS. 4 and 5 illustrate treatments of stenosis 113. In FIG. 4 a dilation balloon 410 has been introduced into blood vessel 110 and advanced to region 112 where it has been expanded as indicated by arrow E. This expansion exerts force on stenosis 113 which causes it to break down. This treatment and others can produce emboli 420 which are fragments of stenosis 113. Member 120 protects emboli 420 from blood flow and prevents them from entering the bloodstream.

As illustrated in FIG. 5, vascular stent 510 may be used to reduce stenosis instead of or in addition to dilation balloon 410. Stent 510 may be any vascular stent or other structure including the examples discussed above. Treatment(s) including multiple stents, interconnected stent, stents which do not touch, stents kept apart by intermediate structures, stent segments, supplemental stents and other structures is also contemplated. FIG. 5 also shows emboli 520 which are isolated by member 120 from blood flow.

Still further treatments are contemplated, for example, administration of drugs, hormones, testing compounds, and other medicaments. Introduction of devices, suturing, anastomosis, cutting, fusing, testing, biopsy, and other operations are also contemplated. Furthermore, laser treatment, heat application, assisted viewing and probing may occur. As used herein "treating" and "treatment(s)" includes, without limitation, the foregoing examples, unless specifically indicated to the contrary.

With reference to FIGS. 6-10 there is illustrated one delivery method and apparatus according to the present invention. Attributes which are the same or similar to those discussed above are indicated with reference numerals which are increased from the 100's to the 600's (e.g. 120 becomes 620). It should be understood that delivery of various other embodiments, including those mentioned above, is also contemplated. It should further be understood that the following procedures could be performed in the order listed or in a variety of other orders, for example, deploying an opposite end first, staggered deployment, fluoroscopically aided deployment, and in still other manners. FIG. 6 shows guidewire 610 which may be any guidewire appropriate for endovascular surgery and may vary according to various treatment indications, including those mentioned above.

With continuing reference to FIG. 6, tubular member 620 and expandable member 630 are shown compressed about guidewire 610. Tip 605 may cover a terminal portion of guidewire 610 and an end portion of member 620. Tip 605 could be a flexible tip, a guiding tip, a cannula or any other tip or tips of differing size, shape and structure. Member 630 and a portion of member 620 are housed within sheath or catheter 640. Sheath or catheter 640 maintains member 630 in a compressed state in the case of a self-expanding stent, for example. Sheath or catheter 640 could also extend to house more of member 620 and guidewire 610 and could extend even further to house some or all of tip 605. As a further option, sheath or catheter 640 could have a tip of its own, for example, a nose cone. In still other embodiments tip 605 may not be present and member 620 could be maintained in place by a dissolvable adhesive, by a low profile removable wrap or other structure, or could be compressed about guidewire 610 where exposure to liquid, e.g. blood, was limited or eliminated until deployment was desired.

With reference to FIGS. 7 and 8 there is illustrated an example of deployment of member 630 and one end of member 620. In FIG. 7 catheter or sheath 640 has been moved relative members 620 and 630. This can be accomplished by advancing guidewire 610 in the direction indicated by arrow G effective to move members 620 and 630 in the same direction, by retracting catheter or sheath 640 in the direction indicted by arrow C, or by a combination of both movements. Other deployment techniques and devices are also contemplated. For example, one or more additional wires, sheaths, catheters, snares, pushers, dilation balloons, or other structures which could move members 620 and 630 and/or catheter or sheath 640 are contemplated.

Regardless of which deployment mode is used, member 630 can expand as it exits catheter or sheath 640. This expansion also causes member 620 to expand with member 630. FIG. 8 illustrates member 630 after it has completely exited catheter or sheath 640 and is fully expanded. In vivo, member 630 can maintain member 620 against the interior surface of a blood vessel as was described above or in another desired position or location.

With reference to FIGS. 9 and 10 there is illustrated deployment of the opposite end of member 620. In FIG. 9, guidewire 610 has been advanced in the direction indicated by arrow T which is effective to move tip 605 in the same direction. During this movement, members 620 and 630 can be maintained in place by force exerted by member 630 against the interior wall of a blood vessel. The result of this movement is shown in FIG. 10 where tip 605 has been advanced completely off of end 622 of member 620 allowing expansion of end 622. Once members 620 and 630 are in the configuration shown in FIG. 10, blood flow can be routed through member 620 to expand member 620 as described above and illustrated in connection with FIGS. 2 and 3. Additional deployment modes for the opposite end of member 620 are also contemplated including, for example, those discussed above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. It should be understood that while features described above may be desirable, they nonetheless may not be necessary and embodiments lacking the same may be contemplated as within the scope of the invention, that scope being defined by the claims that follow. In reading the claims it is intended that when words such as "a," "an," "at least one," "a portion," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A method of both treating a stenosed region of the interior surface of a blood vessel and inducing repair of the region, comprising:
   introducing a device into the blood vessel, the device including a tubular first member at least partially comprised of an extracellular matrix material, said tubular first member having first and second ends, said tubular first member being unsupported between said first end and said second end and having barbs which perforate said tubular first member and enter tissue of the blood vessel;
   inserting said device into said vessel so that said barbs are upstream of said second end of said tubular first member and of said stenosed region and so that said tubular first member shields at least a portion of the stenosed region of the interior surface from blood flow; and
   introducing a dilation balloon into said tubular first member after inserting said device, and inflating at least a portion of said balloon against said unsupported tubular first member so that said balloon expands said unsupported tubular first member and the stenosed region and maintains the stenosis out of blood flow;
   wherein when said balloon has been removed, said unsupported tubular first member remains adjacent with the stenosed region and is effective to induce repair of the stenosed region.

2. The method of claim 1 wherein the inserting includes forming a seal between at least a portion of the device and the vessel and routing flow substantially through the device.

3. The method of claim 1 wherein said tubular member promotes desired remodeling.

4. The method of claim 1 wherein the inserting includes maintaining the first end of the device against the interior surface of the blood vessel, and the portion of said tubular first member that shields at least a portion of the stenosed region extends from substantially the first end to substantially about the second end.

5. The method of claim 1 further comprising isolating a portion of the vessel from the flow.

6. The method of claim 1 wherein the flow is substantially maintained during the shielding.

7. The method of claim 1, wherein said tubular first member remains in the vessel adjacent the stenosis in an unsupported state so as to remodel the interior of the blood vessel.

8. A method for treating a stenosed region in a vascular vessel of a patient, comprising:
   introducing a shielding device into the vascular vessel, the shielding device including a longitudinally unsupported tube of remodelable extracellular matrix material having barbs which perforate the tube;
   attaching the tube of remodelable extracellular matrix material to the vascular vessel with said barbs so that said barbs enter tissue of said vascular vessel and are upstream of the stenosed region;
   shielding the stenosed region of the vascular vessel with the tube of remodelable extracellular matrix material while the tube of extracellular matrix material is attached to the vascular vessel with the barbs;
   introducing a dilation balloon into the tube of remodelable extracellular matrix material while the tube of extracellular matrix material is attached to the vascular vessel with the barbs; and
   expanding the dilation balloon within the longitudinally unsupported tube of remodelable extracellular matrix material so as to expand said tube and the stenosed region.

9. The method of claim 8, wherein the vessel is a blood vessel.

10. The method of claim 8, wherein said expanding presses said longitudinally unsupported tube against the stenosed region, and said tube remains in contact with the stenosed region after deflation and removal of said dilation balloon.

11. The method of claim 10, wherein said longitudinally unsupported tube remains in the vascular vessel in contact with the stenosed region so as to remodel the interior of the vascular vessel.

12. A method for both treating and inducing repair at a stenosed region of a blood vessel, comprising:
   introducing a device into the blood vessel, the device including an unsupported sleeve segment comprised of an extracellular matrix material effective to induce repair of the blood vessel and barbs which perforate the sleeve segment, the blood vessel having an interior surface;
   positioning the unsupported sleeve segment comprised of an extracellular matrix material so as to pass through the stenosed region and shield at least a portion of the interior surface of the blood vessel on either side of the stenosed region from blood flow, with said barbs entering tissue of the blood vessel upstream of the stenosed region; and
   after said positioning the unsupported sleeve segment, positioning a dilation balloon at the stenosed region and within the unsupported sleeve segment comprised of an extracellular matrix material; and expanding the dilation balloon to an expanded state while positioned at the stenosed region so as to force the unsupported sleeve segment comprised of an extracellular matrix material against the stenosed region and dilate said sleeve segment and the stenosed region;

wherein while the dilation balloon is in the expanded state, the unsupported sleeve segment comprised of an extracellular matrix material is effectively positioned to trap emboli generated during said expanding; and wherein after said expanding, the unsupported sleeve segment comprised of extracellular matrix material remains in the blood vessel so as to induce repair of the blood vessel at the stenosed region.

13. A method of both treating a stenosed region of the interior surface of a blood vessel and inducing repair of the region, comprising:

introducing a device into the blood vessel, the device including a tubular first member at least partially comprised of an extracellular matrix material, said tubular first member having first and second ends, said tubular first member being unsupported between said first end and said second end;

inserting said device into said vessel so that said tubular first member shields at least a portion of the stenosed region of the interior surface from blood flow; and introducing a dilation balloon into said tubular first member after inserting said device, and inflating at least a portion of said balloon against said unsupported tubular first member so that said balloon expands said unsupported tubular first member and the stenosed region and maintains the stenosis out of blood flow;

wherein when said balloon has been removed, said unsupported tubular first member remains adjacent with the stenosed region and is effective to induce remodeling of the stenosed region.

14. The method of claim 13, wherein said inflating results in breaking of at least part of the stenosis.

15. The method of claim 14, wherein said breaking results in pieces of the stenosis being released from the stenosis and held between said unsupported tubular first member and the interior surface of the blood vessel.

16. The method of claim 13, wherein said unsupported tubular member remains against the interior surface of the blood vessel and covering the stenosis until the interior surface is remodeled.

* * * * *